(12) United States Patent
Kangas

(10) Patent No.: US 10,456,361 B2
(45) Date of Patent: Oct. 29, 2019

(54) RAPIDLY DEGRADING EMBOLIC PARTICLES WITH THERAPEUTIC AGENT RELEASE

(71) Applicant: Boston Scientific Scimed, Inc., Maple Grove, MN (US)

(72) Inventor: Steven L. Kangas, Woodbury, MN (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 89 days.

(21) Appl. No.: 14/614,928

(22) Filed: Feb. 5, 2015

(65) Prior Publication Data

US 2015/0231075 A1   Aug. 20, 2015

Related U.S. Application Data

(60) Provisional application No. 61/939,794, filed on Feb. 14, 2014.

(51) Int. Cl.
| | | |
|---|---|---|
| *A61K 9/14* | (2006.01) | |
| *A61K 31/337* | (2006.01) | |
| *A61K 47/34* | (2017.01) | |
| *A61K 47/36* | (2006.01) | |
| *A61K 47/44* | (2017.01) | |

(52) U.S. Cl.
CPC ............. *A61K 9/14* (2013.01); *A61K 31/337* (2013.01); *A61K 47/34* (2013.01); *A61K 47/36* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,439,686 A | 8/1995 | Desai et al. | |
| 5,916,596 A * | 6/1999 | Desai | A23L 1/296 |
| | | | 424/439 |
| 2009/0169471 A1 * | 7/2009 | Richard | A61K 9/0019 |
| | | | 424/1.29 |
| 2011/0015664 A1 | 1/2011 | Kangas et al. | |
| 2011/0217379 A1 | 9/2011 | Wang et al. | |

FOREIGN PATENT DOCUMENTS

| | | | |
|---|---|---|---|
| CN | 101889982 A | 11/2010 | |
| EP | 0717041 | 6/1996 | |
| WO | 9814174 | 4/1998 | |
| WO | 2003022264 A1 | 3/2003 | |
| WO | WO 03022264 A1 * | 3/2003 | ........... A61K 9/0019 |
| WO | 2010086863 A2 | 8/2010 | |
| WO | 2013181022 A1 | 12/2013 | |
| WO | WO 2013181022 A1 * | 12/2013 | ............. A61K 9/146 |

OTHER PUBLICATIONS

Mandala, M.; Falanga, A.; Roila, F. Management of venous thromboembolism (VTE) in cancer patients: ESMO Clinical Practice Guidelines, Annals of Oncology, 22, 2011, vi85-vi92.*
Alex Sparreboom et al., "Comparative Preclinical and Clinical Pharmacokinetics of a Cremophor-Free, Nanoparticle Albumin-Bound Paclitaxel (ABI-007) arid Paclitaxel Formulated in Cremophor (Taxol)," Clin Cancer Res 2005; 11(11) Jun. 1, 2005, 4136-4143.
Patricia B. Malafaya et al., "Starch-based microspheres produced by emulsion crosslinking with a potential media dependent responsive behavior to be used as drug delivery carriers," J Mater Sci: Mater Med (2006) 17: 371-377.
Sung Wook Shin, "The Current Practice of Transarterial Chemoembolization for the Treatment of Hepatocellular Carcinoma," Korean J Radiol 10(5), Sep./Oct. 2009, 425-434.
Nuhad K Ibrahim et al., "Phase I and Pharmacokinetic Study of ABI-007, a Cremophor-fee, Protein-stabilized, Nanoparticle Formulation of Paclitaxel", Departments of Breast Medical Oncology, May 1, 2002, vol. 8, 1038-1044.
International Search Report and Written Opinion dated Feb. 14, 2014, for PCT/US2015/014593 (9 pages).

* cited by examiner

*Primary Examiner* — Jessica Worsham

(57) ABSTRACT

In accordance with one aspect, embolic particles are provided which comprise sub-particles that comprise a therapeutic agent of low solubility dispersed in a matrix that comprises a biodegradable polymer. Other aspects pertain to injectable compositions that comprise such particles and to methods of treatment that employ such injectable compositions. Still other aspects pertain to methods of making such particles.

6 Claims, 3 Drawing Sheets

RAPIDLY DEGRADING EMBOLIC PARTICLES WITH THERAPEUTIC AGENT RELEASE

FIELD OF THE INVENTION

The invention relates to polymeric embolic particles for injection that exhibit therapeutic agent release.

BACKGROUND OF THE INVENTION

Many clinical situations benefit from regulation of the vascular, lymphatic or duct systems by restricting the flow of body fluid or secretions. For example, the technique of embolization involves the introduction of particles into the circulation to occlude blood vessels, for example, so as to either arrest or prevent hemorrhaging or to cut off blood flow to a structure or organ. Temporary occlusion of blood vessels is desirable for managing various diseases and conditions.

In one example of an embolization procedure, local anesthesia is first given over a common artery. The artery is then percutaneously punctured and a catheter is inserted and fluoroscopically guided into the area of interest. An angiogram is then performed by injecting contrast agent through the catheter. An embolic agent is then deposited through the catheter. The embolic agent is chosen, for example, based on the size of the vessel to be occluded, the desired duration of occlusion, and/or the type of disease or condition to be treated (e.g., hypervascular tumors, uterine fibroids, etc.), among others factors. A follow-up angiogram may be performed to determine the specificity and completeness of the arterial occlusion. Blocking the blood supply to the tissue is intended to result in shrinkage and/or death of the tissue.

Embolic therapy is currently used to treat late stage liver cancer for patients that are not candidates for liver transplantation or liver resection. There are currently a number of specific embolic therapies available. These therapies include bland embolization, transarterial chemoembolization (TACE) and drug eluting bead (DEB) therapy.

Bland embolization utilizes embolic particles injected into arteries feeding the tumor to stop blood flow to the tumor, thus causing necrosis. The embolic particles do not contain a drug.

TACE involves initial localized injections of a chemotherapeutic drug followed immediately by injection of embolic particles to prevent drug reflux and to cause embolization. TACE provides two modes of action, embolization (necrosis) and chemotherapy, and it is more effective than BLAND embolization. However with TACE there is a lack of sustained drug release since it involves a single injection of a drug. In addition TACE is cumbersome to perform since it involves two separate steps in the procedure.

DEB combines the drug into the embolic particles and like TACE involves two modes of action. Unlike TACE, DEB offers the potential for sustained drug release. However, currently available DEB products show in-vitro rapid release (i.e., within hours) of the drug from the embolic particles. Also, current DEB therapy utilizes biostable particles so re-treatment is not possible. Clinically, DEB has been shown to be somewhat superior in efficiency to TACE. None of the embolic therapies is currently curative, although in a majority of cases a single therapy delays tumor progression.

SUMMARY OF THE INVENTION

In accordance with one aspect of the invention, embolic particles are provided, which comprise therapeutic-agent-containing sub-particles dispersed in a biodegradable polymer matrix. The embolic particles are configured such that, upon administration to a body lumen of a subject, the biodegradable polymer matrix degrades, leading to the release of the sub-particles. In some embodiments, the sub-particles are also configured such that the sub-particles remain localized at the injection site for a period of time after the biodegradable polymer matrix completely degrades.

Other aspects of the invention pertain to injectable compositions that comprise such particles and to methods of treatment that employ such injectable compositions.

Still other aspects of the invention pertain to methods of making such particles.

These and various additional aspects and embodiments of the present invention will become immediately apparent to those of ordinary skill in the art upon review of the Detailed Description and any appended claims to follow.

DETAILED DESCRIPTION

Figures 1A, 1B, 1C:
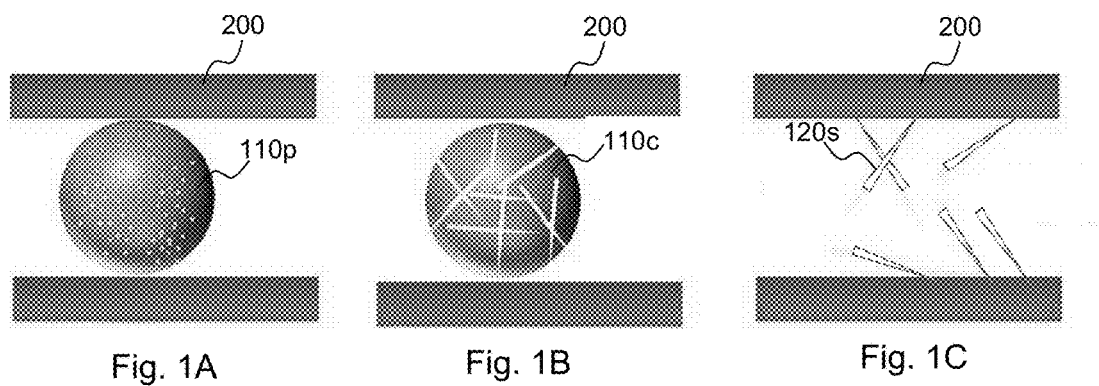
FIGS. 1A-1C are schematic illustrations of three states of an embolic particle in a vessel as a function of time, in accordance with an embodiment of the present invention.

In some aspects, the present disclosure provides therapeutic-agent-releasing embolic particles that are capable of embolizing arteries in a tumor before rapidly degrading. In certain beneficial embodiments, the particle persists long enough to cause tumor necrosis while at the same time degrading quickly enough to avoid significant vessel thrombosis, thereby leaving open the possibility of a subsequent embolic treatment at the same site. In certain beneficial embodiments, the embolic particles provide extended therapeutic agent release long after degradation.

In accordance with various embodiments, the present disclosure provides embolic particles that comprise therapeutic-agent-containing sub-particles dispersed in a biodegradable polymer matrix. The embolic particles are configured such that, upon administration to a body lumen of a subject, the biodegradable polymer matrix degrades, leading to the release of the sub-particles.

For example, the embolic particles may be configured such that upon administration to a body lumen of a subject (e.g., a blood vessel such as an artery, etc.), the biodegradable polymer degrades at a rate that is sufficiently slow to embolize the vessel and cause necrosis of downstream tissue (e.g., embolizing the vessel for at least 60 minutes), while at the same time degrading at a rate that is sufficiently rapid to restore blood flow in the vessel within 48 hours of administration, more preferably within 36 hours of administration, so as to reduce the likelihood of thrombosis.

In various embodiments, the therapeutic agent continues to be released locally after the degradation of the biodegradable polymer matrix, for example, continuing to be released for an extended time (i.e., at for at least 7 days, up to 1 month, or more) after the biodegradable polymer matrix has completely degraded. For example, the embolic particles may contain therapeutic-agent-containing sub-particles at least a portion of which are configured to remain localized at the embolism site and continue to release therapeutic agent for an extended time after complete degradation of the biodegradable polymer matrix.

As defined herein, "complete degradation" is the point where 10 wt % or less, preferably 5 wt % or less, even more preferably 2 wt % or less, of the original biodegradable polymer weight (i.e., the biodegradable polymer weight at the time of injection) remains at the embolism site.

In this regard, it is desirable to re-establish blood flow after the embolic particle causes necrosis, so that the vessel can be re-treated at a later time. Stoppage of blood flow to the tumor only needs to occur for a short period of time to result in tumor necrosis, after which blockage is no longer needed and, in fact, interferes with the application of additional therapy to the same site. In many cases, however, it is beneficial to provide extended localized therapeutic agent release to the tumor, which normally is not possible with rapidly degrading particles, because the therapeutic agent is released and carried downstream from the site. In certain embodiments, the present disclosure provides therapeutic-agent-containing sub-particles that are configured to remain localized at the embolism site, thereby overcoming the conundrum of designing a fast-degrading particle with sustained therapeutic agent delivery.

The injectable particles may be used to treat various diseases and conditions in a wide variety of subjects. Subjects include vertebrate subjects, particularly humans and various warm-blooded animals, including pets and livestock. As used herein, "treatment" refers to the prevention of a disease or condition, the reduction or elimination of symptoms associated with a disease or condition, or the substantial or complete elimination of a disease or condition.

The injectable particles of the disclosure may vary in shape. In certain embodiments, they are substantially spherical, for example, having the form of a perfect (to the eye) sphere or the form of a near-perfect sphere such as a prolate spheroid (a slightly elongated sphere) or an oblate spheroid (a slightly flattened sphere), among other regular or irregular near-spherical geometries. In embodiments where the particles are substantially spherical, at least half of the particles (50% or more, for example, from 50% to 75% to 90% to 95% or more of a particle sample) may have a sphericity of 0.8 or more (e.g., from 0.80 to 0.85 to 0.9 to 0.95 to 0.97 or more). The sphericity of particles can be determined, for example, using a Beckman Coulter RapidVUE Image Analyzer version 2.06 (Beckman Coulter, Miami, Fla.). Briefly, the RapidVUE takes an image of continuous-tone (grayscale) form and converts it to a digital form through the process of sampling and quantization. The system software identifies and measures the particles in an image. The sphericity of a particle, which is computed as Da/Dp (where $Da=\sqrt{(4A/\pi)}$; $Dp=P/\pi$; $A$=pixel area; $P$=pixel perimeter), is a value from zero to one, with one representing a perfect circle. A particle is "spherical" if it has a sphericity of 0.8 or more (e.g., from 0.80 to 0.85 to 0.9 to 0.95 to 0.97 or more).

The injectable particles of the present disclosure can vary significantly in size, with typical widths (e.g., the diameter of a sphere, the diameter of a rod or fiber, etc.) of the particles ranging, for example, from 10 to 1000 microns (μm) (e.g., from 10 to 20 to 50 to 100 to 150 to 200 to 500 to 1000 microns), more typically from 20 to 200 microns.

Therapeutic-agent-containing sub-particles for use in the embolic particles of the present disclosure may vary significantly in size, with typical widths (e.g., the diameter of a sphere, the diameter of a rod or fiber, etc.) of the sub-particles being less than the width of the embolic particle that they occupy, more typically less than 0.5 times, less than 0.1 times, less than 0.03 times, less than 0.01 times, less than 0.003 times, or even less than 0.001 times the width of the embolic particle.

In various embodiments, the sub-particles may range, for example, from 10 nm to 10,000 nm in width (e.g., from 10 nm to 25 nm to 50 nm to 100 nm to 250 nm to 500 nm to 1000 nm to 2500 nm to 5,000 nm to 10,000 nm in width), among other values.

In various embodiments, the sub-particles are needle-like particles which have an aspect ratio (length:width) ranging from 10:1 to 25:1 to 50:1 to 100:1 to 250:1 to 500:1 to 1000:1 or more. In some of these embodiments, the length of such sub-particles may be on the order of the width of the embolic particle, ranging, for example, from 0.1 times to 0.25 times to 0.5 times to 1.0 times the width of the embolic particle, or more.

As used herein, "polymers" are molecules that contain multiple copies of one or more types of constitutional species, commonly referred to as monomers. The number of monomers within a given polymer may vary widely, ranging, for example, from 5 to 10 to 25 to 50 to 100 to 1000 to 10,000 or more constitutional units.

As used herein, a polymer is "biodegradable" if it undergoes bond cleavage along the polymer backbone in vivo, regardless of the mechanism of bond cleavage (e.g., enzymatic breakdown, hydrolysis, oxidation, etc.).

Beneficial biodegradable polymers for use in the embolic particles of the present disclosure include (a) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride], poly[1,3-bis(p-carboxyphenoxy)hexane anhydride], and poly(sebacic acid-co-1,3-bis(p-carboxyphenoxy) propane), among others, (b) poly(ortho ester) homopolymers and copolymers, including as class I poly(ortho esters), class II poly(ortho esters), class III poly(ortho esters), and class IV poly(ortho esters), among others, and (c) polysaccharides homopolymers and copolymers such as starch and alginates, among others.

The injectable particles of the present disclosure may be non-crosslinked or they may be covalently and/or non-covalently crosslinked. Thus, in some embodiments, crosslinking agents such as covalent crosslinking agents or ionic crosslinking agents may be present in the injectable particles, whereas in other embodiments crosslinking agents are absent from the particles. In some embodiments the particles may be crosslinked by exposure to radiation (e.g., gamma or e-beam radiation), which may occur in conjunction with sterilization of particles.

Beneficial therapeutic agents for use in the embolic particles of the present disclosure include anti-tumor agents. Beneficial therapeutic agents for use in the embolic particles of the present disclosure include those having low solubility therapeutic agents (i.e., having a solubility of less than 1 g/l in water at 25° C., and less than 100 mg/l in some embodiments). Particularly beneficial are low solubility anti-tumor agents such as paclitaxel, everolimus, and sorafenib, among others. Typical therapeutic agent loadings range, for example, from 0.1 wt % or less, to 0.2 wt % to 0.5 wt % to 1 wt % to 2 wt % to 5 wt % to 10 wt % to 20 wt % or more of the dry weight of the composition.

Several embodiments using starch as a biodegradable polymer and paclitaxel as a therapeutic agent will now be discussed. It should be noted that, although a polysaccharide (i.e., starch) is used in discussing various embodiments to follow, other biodegradable polymers are suitable for the practice of the present disclosure. It should also be noted that, although paclitaxel is used in the various embodiments to follow, other therapeutic agents are suitable for the practice of the present disclosure.

Starch is known to biodegrade by an enzymatic process involving amylase. The time of complete degradation for starch embolic particles may be less than two days, for example, ranging from 1 hr to 2 hrs to 4 hrs to 6 hrs to 12 hrs to 18 hrs to 24 hrs to 36 hrs to 48 hrs. Processes to prepare starch microspheres are known in the literature. See, e.g., Patricia B. Malafaya et al., J Mater Sci: Mater Med (2006) 17: 371-377.

In certain embodiments of the present disclosure, a water-in-oil emulsion is formed in which starch is dissolved in an aqueous phase that is dispersed in an oil phase. Amorphous paclitaxel sub-particles or crystalline anhydrous paclitaxel sub-particles may also be dispersed in the aqueous phase. (As discussed below, both amorphous and crystalline anhydrous paclitaxel particles can coalesce over time in the presence of water into needle-like dihydrate crystals. So long as the exposure of the amorphous or crystalline anhydrous paclitaxel particles to water is kept to a reasonable time period, e.g., less than 1 hour, significant crystallization of the amorphous paclitaxel particles or conversion of the crystalline anhydrous paclitaxel particles to crystalline dihydrate paclitaxel particles may be avoided; one can also reduce the processing temperatures to inhibit crystallization.) Water-in-oil emulsion formation may be enhanced by the addition of a surfactant, for example, a non-ionic surfactant such as Tween 80, Span 80, or a suitable low molecular weight polymer such as polyvinyl alcohol or polyvinylpyrrolidone, among others. A homogenizer or sonicator can be used to reduce the dispersed phase to a desired size. A crosslinking agent such as trisodium trimetaphosphate (TSTP), epichlorohydrin, glutaraldehyde or formaldehyde, among others, may be added to crosslink the starch in the dispersed aqueous phase and form embolic particles. For TSTP, the crosslinking reaction is initiated by raising the pH with a suitable basic solution (e.g., a NaOH solution) to activate the crosslinking agent. The reaction is stopped by the addition of a suitable acidic solution (e.g., an HCl solution). Regardless of the method of formation, once formed, the embolic particles, which contain a dispersion of amorphous or crystalline anhydrous paclitaxel sub-particles in a starch matrix, may then be washed, isolated, sized and lyophilized, as desired.

Sub-particles of amorphous paclitaxel may be obtained, for example, by first providing a solution of paclitaxel in a first solvent that is a good solvent for paclitaxel (e.g., tetrahydrofuran, dimethylformamide, dichloromethane, etc.), and then adding drops of this solution into a second solvent that is miscible with the first solvent but which is a poor solvent for paclitaxel (e.g., heptane, hexane, toluene, etc.), with the result being that the paclitaxel precipitates out of solution. To aid in particle dispersibility, a surfactant such as Span 80 may be added to the particles.

Sub-particles of as received crystalline anhydrous paclitaxel may be formed by milling of the as received crystalline anhydrous powder in a high frequency shaker with zirconium milling media.

Figure 4:
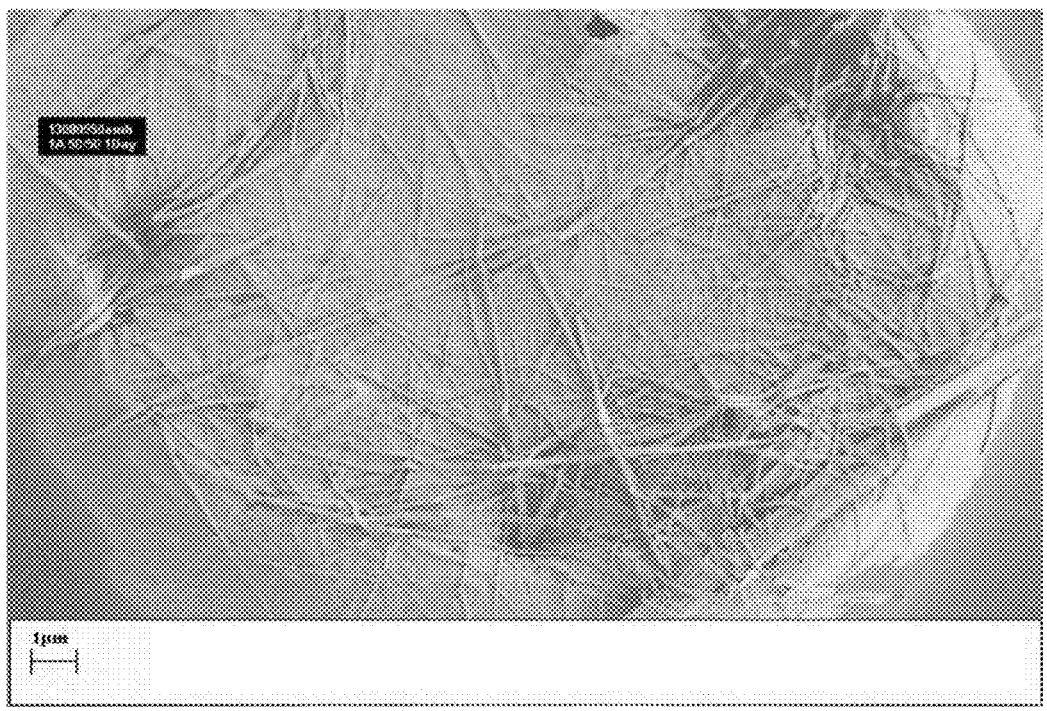
FIG. 4 is a micrograph of a PLGA embolic particle, which contains dihydrate crystals.

It has been observed that for particles containing amorphous paclitaxel microparticles dispersed in a polymer matrix (i.e., PLGA), upon incubation in water at 37 C, the amorphous paclitaxel particles coalesce within hours into large, needle-like dihydrate crystals. An example of crystalline paclitaxel formation in a PLGA particle is shown in FIG. 4 (scale=1 micron).

Figure 5:
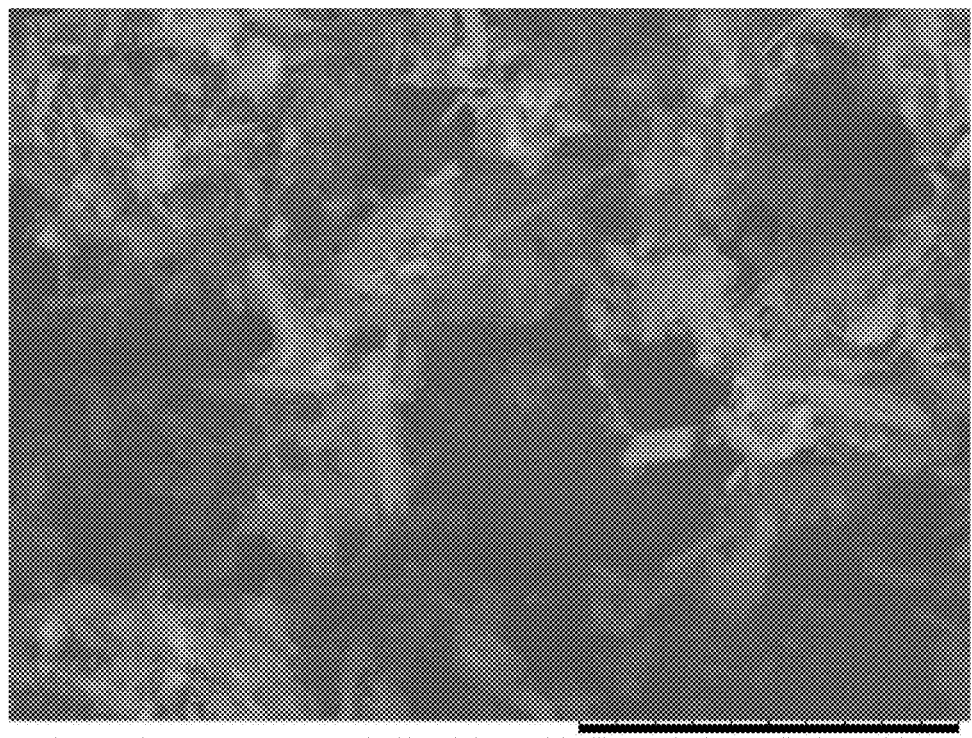
FIG. 5 is a micrograph of as received as-received crystalline anhydrous paclitaxel powder.
Figure 6:
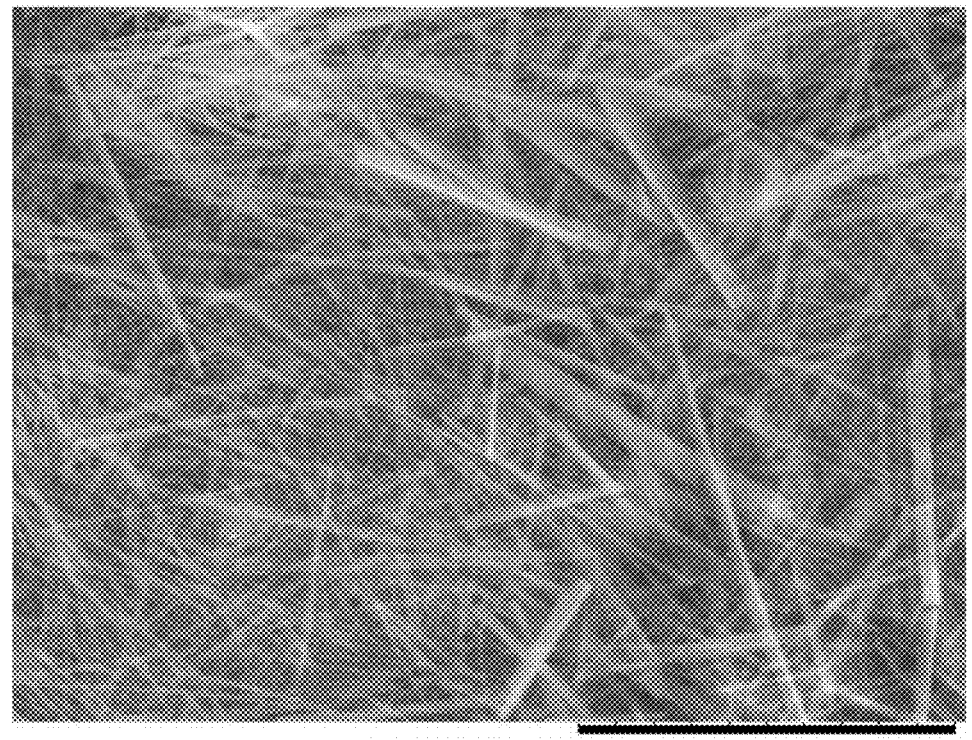
FIG. 6 is a micrograph of the crystalline anhydrous paclitaxel powder of FIG. 5 after incubation overnight in water at 37° C.

It has also been observed that for as-received crystalline anhydrous paclitaxel powder dispersed in water at 37° C., the crystalline anhydrous paclitaxel particles coalesce within hours to large needle-like dihydrate crystals. Examples of as-received crystalline anhydrous paclitaxel powder, and crystalline dihydrate formed after incubation of the crystalline anhydrous paclitaxel powder overnight in water at 37° C., are shown in FIGS. 5 and 6, respectively.

Regardless of the method by which the amorphous or crystalline dihydrate paclitaxel sub-particles are dispersed within the starch matrix, upon introduction to an aqueous in vivo environment (e.g., injection into a patient), water will be available over a time sufficient for dihydrate formation, and the amorphous or crystalline anhydrous paclitaxel microparticles within the embolic particles may coalesce into needle-like dihydrate crystals.

As additional time passes in vivo, the starch is broken down leaving needle-like dihydrate crystals behind in the blood vessel. Crystalline dihydrate paclitaxel is very lipophilic (aqueous solubility <1 g/L), and the dihydrate crystalline polymorph can act as a drug depot due to its slow dissolution profile, which can transpire over the course of about a month.

Use of such particles is shown schematically in FIGS. 1A-1C. When an embolic particle 110p is injected into an artery (e.g., an artery 200 feeding a tumor) as shown in FIG. 1A, the particle 110p stops blood flow to the tissue (e.g., tumor tissue) downstream of the embolic particle, causing tumor necrosis. Upon being exposed to water in the artery, the amorphous or crystalline anhydrous paclitaxel in the particles starts to convert to dihydrate crystal forming an embolic particle 100c with crystalline paclitaxel needles as shown in FIG. 1B. When the starch particle degrades as shown in FIG. 1C, at least a portion of the crystalline paclitaxel needles 120s remain in the vasculature, thereby acting as drug depot and providing sustained drug release to the tumor while blood flow is restored.

Alternatively, dispersed amorphous or crystalline anhydrous paclitaxel within the embolic particles can be subjected to a vapor annealing in ethanol ex vivo to efficiently convert the amorphous or crystalline anhydrous paclitaxel to dihydrate crystals. In this way, one does not have to rely on in-vivo conversion of amorphous or crystalline anhydrous paclitaxel to dihydrate crystals. A suitable vapor annealing process is described in U.S. Patent Application Pub. No. 2011/0015664 A1 to Kangas et al.

In other embodiments of the present disclosure, embolic particles are formed, in which oil sub-particles are dispersed throughout the biodegradable polymer (e.g., starch) matrix. The oil sub-particles may contain, for example, therapeutic agent nanoparticles (e.g., crystalline paclitaxel nanoparticles) dispersed in a suitable oil, for example, an iodinated oil such as an iodinated plant-based oil or an iodinated animal-based oil. In a particular embodiment, Lipiodol®

(also known as ethiodized oil and Ethiodol®) may be employed. Lipiodol is an iodinated poppy seed oil, which is used as a contrast agent. Lipiodol is also known to have high affinity to liver tumors (see, e.g., Sun Wook Shin, *Korean J Radiol* 10(5), September/October 2009, 425-434) with residence time in the tumor of weeks (as observed by fluoroscopy), and it is commonly used as a contrast agent in TACE procedures. In the present disclosure, nanoparticles of therapeutic agent (e.g., crystalline paclitaxel nanoparticles) are dispersed in lipiodol, which is, in turn, dispersed in a starch matrix. Typical sizes for the nanoparticles of therapeutic agent range, for example, from 5 to 500 nm (e.g., from 5 nm to 10 nm to 25 nm to 50 nm to 100 nm to 250 nm to 500 nm), among other possibilities. The oil acts as a tumor specific carrier of the therapeutic agent nanoparticles. As the starch degrades, it releases the oil microspheres. One portion of the oil microspheres may wash downstream and lodge/adsorb in the microvasculature (vessels <10 um diameter) while another portion of the oil microspheres may be deposited on the artery in proximity to where the embolic particle degrades, thereby allowing for sustained release (e.g., days to weeks) of therapeutic agent from the oil into the tissue.

Crystalline dihydrate paclitaxel nanoparticles in lipiodol can be formed by a milling process. Starting with as-received crystalline anhydrous paclitaxel powder from Indena USA Inc., Seattle Wash., USA, the crystalline anhydrous paclitaxel is treated with water to convert to the stable crystalline dihydrate form. Then the crystalline dihydrate paclitaxel and lipiodol from Guerbet LLC, Bloomington, Ind., USA are milled with zirconia milling media using a high speed shaker. Sub-particles of the resulting paclitaxel-containing lipiodol can be formed in an aqueous phase (e.g., starch dissolved in water) by combining the paclitaxel-containing lipiodol with a volume of the aqueous phase and emulsifying the mixture, for example, using a homogenizer or sonicator, forming an oil-in-water emulsion. This composition may then be added to a volume of a suitable oil phase and emulsified, for example, using a homogenizer or sonicator, forming an oil-in-water-in-oil double emulsion. The starch in the dispersed aqueous phase may be cross-linked (e.g., as described above). Regardless of the method of formation, once formed, the embolic particles, which contain a dispersion of therapeutic-agent-containing iodinated oil sub-particles in a starch matrix, may then be washed, isolated, sized and lyophilized, as desired.

Figures 2A, 2B:
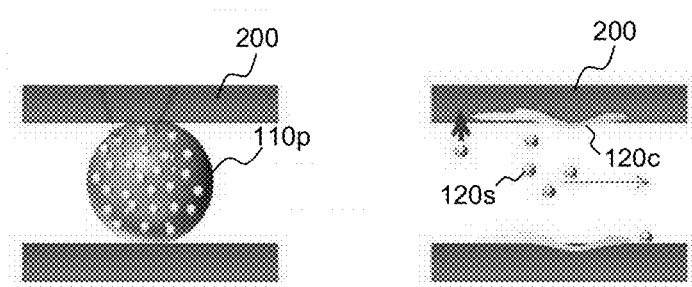
FIGS. 2A-2B are schematic illustrations of two states of an embolic particle in a vessel as a function of time, in accordance with an embodiment of the present invention.

The use of such embolic particles is shown schematically in FIGS. 2A-2B. When the embolic particles 110p are injected into an artery 200 (e.g., an artery feeding a tumor) the particle stops blood flow to the tumor as shown in FIG. 2A, causing tumor necrosis. When the starch in the embolic particle 110p degrades as shown in FIG. 2B, blood flow is restored. Degradation of the starch in the embolic particle 110p also results in the release of the lipiodol sub-particles 120s containing the crystalline paclitaxel nanoparticles, and at least a portion of the sub-particles 120s may form deposits 120c on the artery wall 200 in proximity to the position where the starch particle degraded, allowing for sustained release of paclitaxel from the oil into the surrounding tumor. Other sub-particles may flow downstream and lodge in microvasculature where paclitaxel is also released into the tumor tissue.

Figure 3:
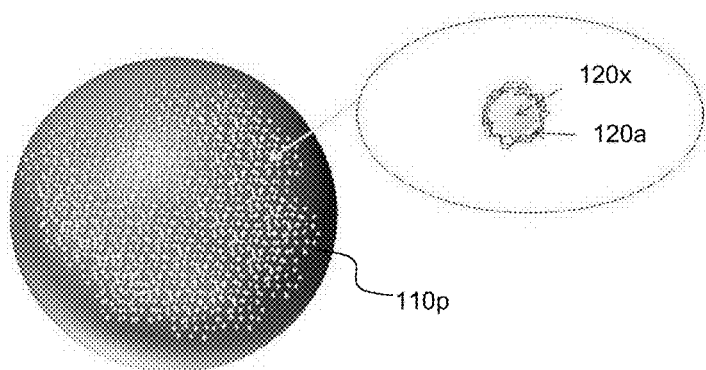
FIG. 3 is a schematic illustration of an embolic particle, and a magnified schematic illustration of one of its sub-particles, in accordance with an embodiment of the present invention.

Referring now to FIG. 3, according to another embodiment of the present disclosure, starch particles 110p are prepared which contain protein stabilized therapeutic agent sub-particles, more particularly, paclitaxel nanoparticles 120x stabilized with albumin 120a. Other proteins that can be used are gelatin and plant based proteins such as gliadin, legumin, soy protein isolate and whey protein isolate, among others. The FDA approved drug Abraxane is an aqueous dispersion of albumin stabilized paclitaxel nanoparticles (mean diameter ~130 nm). Pre-clinical and clinical studies of IV infusion of Abraxane have shown that tumor uptake of paclitaxel is significantly greater than that of a standard cremophor/paclitaxel IV infusion (see, e.g., A. Sparreboom et al., *Clin Cancer Res* 2005; 11:4136-4143). This is believed to be due in part to favorable binding of the albumin to tumor proteins. By incorporating albumin stabilized paclitaxel into starch particles one is able to both embolize the tumor (leading to necrosis) and provide for a much higher localized dose of paclitaxel than is possible with systemic infusion of albumin-stabilized paclitaxel particles. Particles may be formed by creating a water-in-oil emulsion in which the aqueous phase contains dissolved starch and dispersed albumin-stabilized paclitaxel particles. Upon forming an emulsion in which the aqueous phase is dispersed in an oil phase, the starch in the dispersed aqueous phase is crosslinked (e.g., as described above), thereby forming embolic particles. Regardless of the method of formation, once formed, the embolic particles, which comprise a dispersion of protein-stabilized therapeutic agent particles (e.g., albumin-stabilized paclitaxel particles) in a starch matrix, may then be washed, isolated, sized and lyophilized, as desired.

In certain embodiments, the particles of the present disclosure will optionally include imaging contrast agents in amounts useful to enhance in vivo imaging of the particles. (It is noted that some of the embolic particles described above will inherently contain a contrast agent in the form of lipiodol.) Examples of imaging agents include (a) contrast agents for use in conjunction with magnetic resonance imaging (MRI), including contrast agents that contain elements with relatively large magnetic moment such as Gd(III), Dy(III), Mn(II), Fe(III) and compounds (including chelates) containing the same, such as gadolinium ion chelated with diethylenetriaminepentaacetic acid, and (b) contrast agents for use in connection with x-ray fluoroscopy, including metals, metal salts and oxides (particularly bismuth salts and oxides), and iodinated compounds, among others.

The embolic particles of the present disclosure may be stored and transported in wet or dry form, and are preferably stored and transported in a sterile dry form. In addition to biodegradable embolic particles and optional contrast agent as described herein, embolic particle compositions may also optionally contain additional agents, for example, selected from one or more of the following, among others: (a) tonicity adjusting agents such as sugars (e.g., dextrose, lactose, sucrose, etc.), polyhydric alcohols (e.g., glycerol, propylene glycol, mannitol, sorbitol, etc.) and inorganic salts (e.g., potassium chloride, sodium chloride, etc.), among others, (b) suspension agents including various surfactants, wetting agents, and polymers (e.g., albumen, PEO, polyvinyl alcohol, block copolymers, etc.), among others, and (c) pH adjusting agents including various buffer solutes.

Dry or wet embolic particle compositions may be shipped, for example, in a syringe, catheter, vial, ampoule, or other container. Dry forms may be mixed with a suitable liquid carrier (e.g. sterile water for injection, physiological saline, phosphate buffer, a solution containing an imaging contrast agent, etc.) prior to administration. In this way the concentration of the composition to be injected may be varied as desired by the healthcare practitioner in charge of the procedure. Wet forms (e.g., aqueous suspensions) may also be mixed with a suitable liquid carrier (e.g. sterile water for injection, physiological saline, phosphate buffer, a solution containing contrast agent, etc.) prior to administration, allowing the concentration of administered particles (as well as other optional agents) in the suspension to be reduced prior to injection, if so desired by the healthcare practitioner in charge of the procedure. One or more containers of liquid carrier may also be supplied and shipped, along with the dry or wet particles, in the form of a kit. Kits may also include one or more instruments to assist in delivery such as catheters (e.g., microcatheters), guidewires, and so forth. Kits may also include printed material with one or more of the following: (i) storage information and (ii) instructions regarding how to administer the embolic particles to a subject.

As indicated above, in some embodiments, embolic particles in accordance with the present disclosure may be used in treating solid tumors, such as renal carcinoma, bone tumors and liver tumors, among various others. Embolization may be conducted as an enhancement to chemotherapy or radiation therapy. In other embodiments, the particles may be used to treat benign tumors. For example, fibroids, also known as leiomyoma, leiomyomata or fibromyoma, are the most common benign tumors of the uterus.

The present disclosure also encompasses various methods of administering the particulate compositions of the disclosure to effect embolization. One skilled in the art can determine the most desirable way of administering the particles depending on the type of treatment and the condition of the patient, among other factors. Methods of administration include, for example, percutaneous techniques as well as other effective routes of administration. For example, the particulate compositions of the present disclosure may be delivered through a syringe or through a catheter, for instance, a Tracker® microcatheter (Boston Scientific, Natick, Mass., USA), which can be advanced over a guidewire, a steerable microcatheter, or a flow-directed microcatheter (MAGIC, Balt, Montomorency, France). In some embodiments, anticoagulants such as heparin or warfarin are given to the patient during and immediately post procedure, to reduce the likelihood of thrombus formation at the injection site.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. An embolic particle comprising sub-particles dispersed in a matrix that comprises a biodegradable polymer,
    wherein the sub-particles comprise a therapeutic agent of low solubility,
    (a) wherein said sub-particles comprise elongate particles having an aspect ratio ranging from 10:1 to 1000:1 that comprise said therapeutic agent and/or (b) wherein said sub-particles comprise particles that comprise an anti-tumor agent dispersed in oil,
    wherein upon administration to a blood vessel, the matrix of the embolic particle biodegrades and the sub-particles remain localized in the blood vessel such that they continue to release therapeutic agent locally in the blood vessel after the matrix has completely degraded, and
    wherein said sub-particles comprise said elongate particles having an aspect ratio ranging from 10:1 to 1000:1 that comprise said therapeutic agent.

2. An embolic particle comprising sub-particles dispersed in a matrix that comprises a biodegradable polymer,
    wherein the sub-particles comprise a therapeutic agent of low solubility,
    (a) wherein said sub-particles comprise elongate particles having an aspect ratio ranging from 10:1 to 1000:1 that comprise said therapeutic agent and/or (b) wherein said sub-particles comprise particles that comprise an anti-tumor agent dispersed in oil,
    wherein upon administration to a blood vessel, the matrix of the embolic particle biodegrades and the sub-particles remain localized in the blood vessel such that they continue to release therapeutic agent locally in the blood vessel after the matrix has completely degraded, and
    wherein said sub-particles comprise elongate particles having an aspect ratio ranging from 10:1 to 1000:1 of crystalline paclitaxel dihydrate.

3. A kit comprising:
    (a) an injectable medical composition comprising embolic particles in wet or dry form, said embolic particles comprising sub-particles dispersed in a matrix that comprises a biodegradable polymer,
        wherein the sub-particles comprise a therapeutic agent of low solubility,
        wherein said sub-particles comprise elongate particles having an aspect ratio ranging from 10:1 to 1000:1 that comprise said therapeutic agent and/or wherein said sub-particles comprise particles that comprise an anti-tumor agent dispersed in oil, and
        wherein upon administration to a blood vessel, the matrix of the embolic particle biodegrades and the sub-particles remain localized in the blood vessel such that they continue to release therapeutic agent locally in the blood vessel after the matrix has completely degraded, and
    (b) one or more of the following: (i) a catheter, (ii) a guidewire and (iii) a liquid carrier.

4. The embolic particle of claim 1,
    wherein said biodegradable polymer is selected from polyanhydrides, poly(ortho esters) and polysaccharides,
    wherein upon administration to a blood vessel, the matrix of the particle completely biodegrades within a period of ranging from one hour to two days, and
    wherein the sub-particles remain localized in the blood vessel and continue to release therapeutic agent locally in the blood vessel for a period of at least 7 days after the matrix has completely degraded.

5. The embolic particle of claim 2,
    wherein said biodegradable polymer is selected from polyanhydrides, poly(ortho esters) and polysaccharides,
    wherein upon administration to a blood vessel, the matrix of the particle completely biodegrades within a period of ranging from one hour to two days, and
    wherein the sub-particles remain localized in the blood vessel and continue to release therapeutic agent locally in the blood vessel for a period of at least 7 days after the matrix has completely degraded.

6. The embolic particle of claim 1,
    wherein said biodegradable polymer is selected from polyanhydrides, poly(ortho esters) and polysaccharides, and wherein said sub-particles are paclitaxel crystals in the form of elongate particles having an aspect ratio ranging from 10:1 to 1000:1.

\* \* \* \* \*